United States Patent [19]

Tsushima et al.

[11] Patent Number: 5,607,927
[45] Date of Patent: Mar. 4, 1997

[54] CEPHALOSPORIN DERIVATIVE

[75] Inventors: Masaki Tsushima; Katsuyoshi Iwamatsu; Atsushi Tamura; Seiji Shibahara, all of Kanagawa, Japan

[73] Assignee: Meiji Seika Kaisha, Ltd., Tokyo, Japan

[21] Appl. No.: 385,363

[22] Filed: Feb. 7, 1995

Related U.S. Application Data

[63] Continuation of Ser. No. 30,866, Mar. 12, 1993.

[30] Foreign Application Priority Data

Mar. 12, 1992 [JP] Japan .................................. 4-053885

[51] Int. Cl.$^6$ ........................ C07D 501/36; A61K 31/545
[52] U.S. Cl. ........................ 514/206; 540/225; 540/227; 514/203; 514/205
[58] Field of Search ..................... 540/225, 226, 540/227; 514/206, 203

[56] References Cited

U.S. PATENT DOCUMENTS

| 3,992,377 | 11/1976 | Chauvette et al. | 260/243 C |
|---|---|---|---|
| 4,256,739 | 3/1981 | Woodward et al. | 424/200 |
| 5,247,073 | 9/1993 | Ternanhy et al. | 540/226 |

FOREIGN PATENT DOCUMENTS

| 009008A2 | 3/1980 | European Pat. Off. |
| 0210078 | 1/1987 | European Pat. Off. |
| 495584A2 | 7/1992 | European Pat. Off. |
| 0527686 | 2/1993 | European Pat. Off. |

*Primary Examiner*—John M. Ford
*Attorney, Agent, or Firm*—Sughrue, Mion, Zinn, Macpeak & Seas

[57] ABSTRACT

An aminothiazolyl- or aminothiadiazolyl-cephalosporin derivative represented by the following general formula (I) which has a condensed-ring thio group as a 3-positioned substituent group that contains a thiazolylthio group, an oxazolylthio group or a heterocyclic ring thereof as one of the ring components. The compound according to the present invention has excellent activities to inhibit growth of various bacteria, especially Gram-positive bacteria including methicillin-resistant *Staphylococcus aureus* (MRSA), and therefore, the antibacterial agent comprising, as an active ingredient, the inventive compound can be used as a therapeutic drug for the treatment of various bacterial infections.

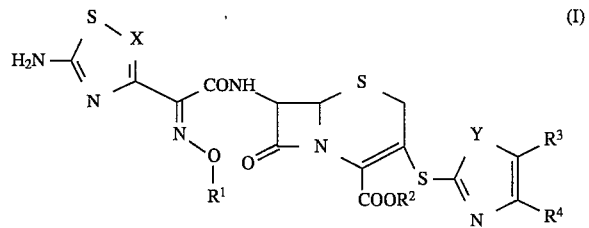

2 Claims, No Drawings

CEPHALOSPORIN DERIVATIVE

This is a Continuation of application Ser. No. 08/030,866, filed on Mar. 12, 1993.

FIELD OF THE INVENTION

This invention relates to a novel cephalosporin derivative which has a condensed-ring thio group as a 3-position substituent group that contains a thiazolylthio group, an oxazolylthio group or a heterocyclic ring thereof as one of the ring components. More particularly, it relates to a cephalosporin derivative which is possessed of a potent antibacterial activity and a profile to give its concentration in blood at a high level.

BACKGROUND OF THE INVENTION

Cephalosporin antibiotics are markedly effective drugs for the treatment of infectious diseases in mammals because of their excellent antibacterial actions and low toxicity against mammals. In recent years, a number of cephalosporin derivatives having an aminothiazolyl-α-(substituted or unsubstituted)hydroxyiminoacetyl group at the 7-position of the cephem ring have been studied and developed because of their potent antibacterial activities and high stability against β-lactamase.

So-called "third generation cephalosporin antibiotics" such as cefotaxime, cefmenoxime and the like are used frequently in most countries of the world, which are characterized by the presence of an aminothiazolyl-α-(substituted or unsubstituted)hydroxyiminoacetyl group at the 7-position of each compound and by their potent antibacterial activities with a broad range of antibacterial spectrum. However, certain compounds of these third generation cephalosporin antibiotics such as cefotaxime, cefmenoxime and the like are still imperfect in terms of their antibacterial activities upon *Pseudomonas aeruginosa* and methicillin-resistant mutants of *Staphylococcus aureus* (hereinafter, referred to as "MRSA") which have recently been causing clinical problems. Especially, MRSA has in recent years been causing trouble of triggering serious bacterial infection-related diseases. In consequence, great concern has been directed toward the development of novel cephalosporin antibiotics having improved anti-bacterial activities upon this methicillin-resistant bacterium.

SUMMARY OF THE INVENTION

The inventors of the present invention have previously reported a cephalosporin derivative (Japanese Patent Application No. 3-226401, U.S. patent application Ser. No. 07/925,035 filed on Aug. 5,1992, and European Patent Application No. 92402278.3) which was developed to resolve the aforementioned problems involved in the prior art. The present inventors have further conducted intensive studies with the aim of providing a novel cephalosporin derivative which has an antibacterial activity similar to or higher than that of the previously reported derivative. As the results, the present inventors have succeeded in synthesizing a novel cephalosporin derivative represented by the following general formula (I) which was capable of exhibiting excellent antibacterial activity and also of giving its concentration in blood at a high level at the time of its administration. It was found also that the compound of the general formula (I) can be administered orally, in addition to its usual route of administration such as subcutaneous, intravenous or the like injection. The present invention has been accomplished on the basis of these findings.

The present invention provides a cephalosporin derivative represented by the following general formula (I) and pharmaceutically acceptable salts thereof:

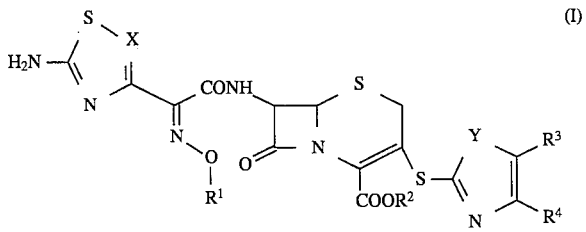

wherein Y is an oxygen atom when X is a carbon atom or Y is a sulfur atom or an oxygen atom when X is a nitrogen atom; $R^1$ is a hydrogen atom, a lower alkyl group or a substituted lower alkyl group; $R^2$ is a hydrogen atom or an ester-forming group which is hydrolyzed by a digestive tract esterase; and $R^3$ and $R^4$ are the same or different groups selected from a hydrogen atom, a halogen atom, a lower alkyl group, a substituted lower alkyl group, a lower alkenyl group, a hydroxyl group, an amino group and a lower alkoxy group, provided that $R^3$ may, taken together with $R^4$, form a cyclic structure, the resulting ring being a saturated cyclic alkyl group, a benzene ring or a heterocyclic ring.

Other objects and advantages of the present invention will be made apparent as the description progresses.

DETAILED DESCRIPTION OF THE INVENTION

In the cephalosporin derivative of the present invention represented by the general formula (I), the alkyl moiety of a lower alkyl group or a lower alkoxy group means a straight- or branched-chain alkyl group having 4 or less carbon atoms, and the term "halogen atom" is intended to include fluorine, chlorine, bromine and iodine atoms.

The ester-forming group indicated by $R^2$ may be any group which is apt to be hydrolyzed by esterase in the living body after administration of the cephalosporin derivative according to the present invention. Examples of such a type of groups include 1-(acyloxy)-(lower)alkyl groups such as pivaloyloxymethyl, acetoxymethyl or 1-acetoxyethyl; 1-(alkoxycarbonyloxy)-(lower)alkyl groups such as 1-(ethoxycarbonyloxy)ethyl or 1-(isopropoxy-carbonyloxy) ethyl; (5-methyl-1,3-dioxolene-4-yl)methyl group; and the like.

Illustrative examples of the cyclic structure formed by the linkage of $R^3$ and $R^4$ include cyclic saturated alkyl groups such as cyclopentane ring or cyclohexane ring; benzene ring; heterocyclic rings each having at least one hetero atom, such as furan ring, tetrahydrofuran ring, pyrrole ring, pyrrolidine ring, piperidine ring, pyridine ring, pirimidine ring or thiophene ring; and the like.

Examples of the cephalosporin derivative of the present invention represented by the general formula (I) are given below by way of illustration and not by way of limitation.

1. 7-{(Z)-2-(2-aminothiazol-4-yl)-2-methoxyiminoacetamido }-3-(benzoxazol-2-yl)thio-3-cephem-4-carboxylic acid
2. 7-{(Z)-2-(5-amino-1,2,4-thiadiazol-3-yl)-2-methoxyiminoacetamido }-3-(benzothiazol-2-yl)thio-3-cephem-4-carboxylic acid
3. 7-{(Z)-2-(5-amino-1,2,4-thiadiazol-3-yl)-2-methoxyiminoacetamido }-3-(thiazolo[5,4-b]pyridin -2-yl)thio-3-cephem-4-carboxylic acid The salts of the compound of the general formula (I) include salts with an alkali metal, e.g., sodium, potassium, etc., an alkaline earth metal, e.g., calcium, magnesium, etc., or an acid, e.g., acetic acid, trifluoroacetic acid, hydrochloric acid, sulfuric acid, etc.

Though the compound of the general formula (I) of the present invention can be produced by various means, it may be convenient to produce it in accordance with a process which comprises 6 steps as diagrammatically shown below with respective reaction formulae.

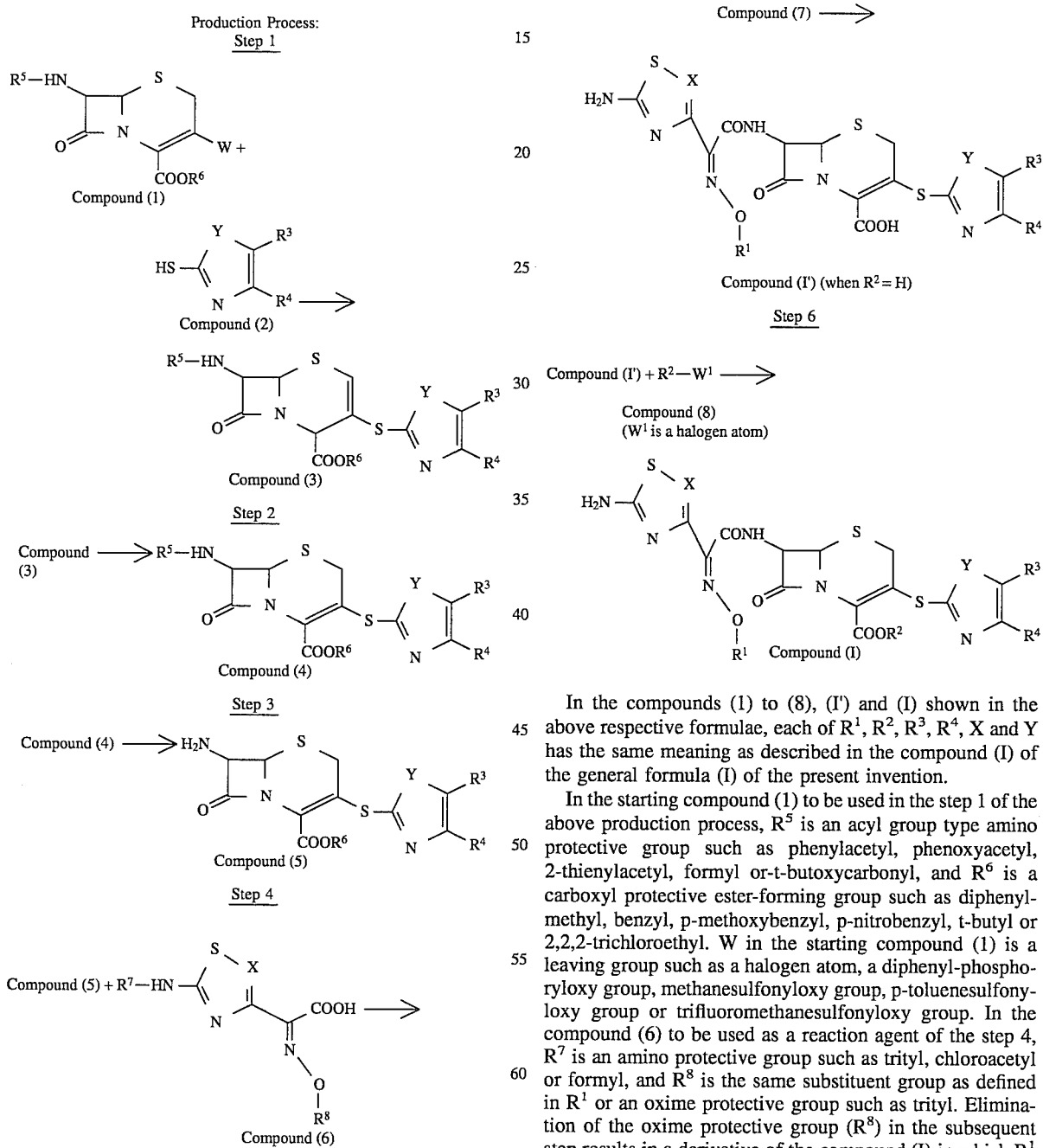

In the compounds (1) to (8), (I') and (I) shown in the above respective formulae, each of $R^1$, $R^2$, $R^3$, $R^4$, X and Y has the same meaning as described in the compound (I) of the general formula (I) of the present invention.

In the starting compound (1) to be used in the step 1 of the above production process, $R^5$ is an acyl group type amino protective group such as phenylacetyl, phenoxyacetyl, 2-thienylacetyl, formyl or t-butoxycarbonyl, and $R^6$ is a carboxyl protective ester-forming group such as diphenylmethyl, benzyl, p-methoxybenzyl, p-nitrobenzyl, t-butyl or 2,2,2-trichloroethyl. W in the starting compound (1) is a leaving group such as a halogen atom, a diphenyl-phosphoryloxy group, methanesulfonyloxy group, p-toluenesulfonyloxy group or trifluoromethanesulfonyloxy group. In the compound (6) to be used as a reaction agent of the step 4, $R^7$ is an amino protective group such as trityl, chloroacetyl or formyl, and $R^8$ is the same substituent group as defined in $R^1$ or an oxime protective group such as trityl. Elimination of the oxime protective group ($R^8$) in the subsequent step results in a derivative of the compound (I) in which $R^1$ is a hydrogen atom.

The following illustratively describes the steps 1 to 6 of the production process shown above with respective reaction formulae.

In the step 1, a starting compound (1) is allowed to undergo a substitution reaction in an anhydrous organic solvent with a compound (2), which has substituent groups $R^3$ and $R^4$, or with a sodium salt of the compound (2) to obtain the compound (3). Preferred examples of the reaction solvent include chloroform, dichloromethane, tetrahydrofuran, N,N-dimethylformamide, acetonitrile, hexamethylphosphate triamide, and the like. Though it depends on the kind of the starting compound (1), solvent and the like to be used, the reaction may be carried out preferably in the presence of a base, especially an organic base such as triethylamine, tributylamine or N,N-diisopropylethylamine. The reaction may be effected at a temperature of preferably from −20° to 10° C. After completion of the reaction, the reaction mixture is subjected to usual after-treatments, for example, a treatment comprising extraction with an organic solvent such as ethyl acetate or methylene chloride, washing the organic layer with water, etc., drying the resulting organic layer on a dring agent such as anhydrous magnesium sulfate, and distilling off the solvent under a rduced pressure, and, if necessary, the thus obtained compound (3) is purified by means of silica gel column chromatography, crystallization and the like.

In the step 2, the 1-positioned sulfur atom in the compound (3) is converted into sulfoxide using an oxidizing agent in an anhydrous organic solvent, and then the oxygen atom is eliminated using a reducing agent, thereby obtaining a compound (4) in which the 2-positioned double bond is rearranged to the 3-position. Preferred examples of the reaction solvent include chloroform, dichloromethane, tetrahydrofuran, N,N-dimethylformamide and the like. More preferably, dichloromethane may be used in the oxidation reaction, and dichloromethane or N,N-dimethylformamide in the reduction reaction. Preferred examples of the oxidizing agent include usually used peracids such as peracetic acid or methachloroperbenzoic acid, as well as potassium permanganate. Examples of the reducing agent include phosphorous halides such as phosphorous trichloride or phosphorous tribromide, as well as trimethylsilyl iodide, acetyl chloride, and stannic chloride. The reaction may be effected at a temperature of preferably from −20° to +50° C., more preferably from −20° to 0° C. After completion of the reaction, the reaction mixture is subjected to ordinary post-treatments and, if necessary, the thus obtained compound (4) is purified by means of silica gel column chromatography, crystallization and the like.

In the step 3, the compound (4) is subjected to a deprotection reaction to eliminate the acyl group ($R^5$) as an amino protective group, thereby obtaining a 7-aminocephem compound (5). The deprotection reaction may be carried out in the ordinary manner for the elimination of the amino protective group ($R^5$). When $R^5$ is a phenylacetyl, phenoxyacetyl, 2-thienylacetyl or the like group, a technique usually used for the elimination of such a type of amino protective group may be employed, in which the compound (4) is allowed to react firstly with phosphorous pentachloride and an organic base and then with an alcohol. The thus obtained 7-aminocephem compound (5) may be purified by means of crystallization or by various chromatographic techniques or used directly in the subsequent step 4 without purifying it.

In the step 4, a compound (7) is obtained by effecting acylation of the 7-positioned amino group of the 7-aminocephem compound (5) using a compound (6) which is an aminothiazolylacetate derivative or an aminothiadiazolylacetate derivative. The acylation reaction may be effected by a usually used means in the field of peptide synthesis chemistry. For example, the compound (7) may be obtained by allowing the 7-aminocephem compound (5) to react with an aminothiazolylacetate or aminothiadiazolylacetate derivative (6), or an activated derivative thereof in the presence of various types of condensing agent. Examples of the condensing agent include dicyclohexylcarbodiimide, Vilsmeier reagent, phosphorous oxychloride and the like. These agents may be selected optionally depending on the reactivity and the like of the compound (5) and the aminothiazolylacetate or aminothiadiazolylacetate derivative (6), or an activated derivative thereof to be used. Preferred examples of the reaction solvent include dichloromethane, chloroform, N,N-dimethylformamide, tetrahydrofuran and the like. The reaction may be carried out at a temperature in the range of from −20° to +50° C., preferably from −20° to 0° C. After completion of the reaction, the reaction mixture is subjected to ordinary post-treatments and, if necessary, the thus obtained compound (7) is purified by means of silica gel column chromatography and the like.

In the step 5, protective groups $R^6$, $R^7$ and $R^8$ of the compound (7) are eliminated by deprotection to obtain a compound (I') whose $R^2$ is a hydrogen atom, as a member of the compound of the present invention represented by the general formula (I). In this instance, the deprotection reaction for the elimination of the groups $R^6$, $R^7$ and $R^8$ may be carried out in the ordinary manner for the elimination of the used protective groups $R^6$, $R^7$ and $R^8$ in any optional order. When the groups $R^6$, $R^7$ and $R^8$ can be deprotected under an acidic condition, the compound (7) may be treated with trifluoroacetic acid, formic acid, hydrochloric acid or the like. When part or all of the groups $R^6$, $R^7$ and $R^8$ can be eliminated under a reduction condition, the compound (7) may be treated by catalytic reduction using various types of catalyst or with a metallic reducing agent such as zinc. Also, when $R^7$ is a chloroacetyl group, it can be eliminated by allowing the compound (7) to react with various types of thioamide. The thus obtained compound (I') can be crystallized and precipitated from its aqueous solution by adjusting pH of the solution. The compound (I') can be purified by means of a chromatography in which a nonionic macroporous resin is used or a gel filtration in which Sephadex or the like is used.

In the step 6, a member of the compound (I) of the present invention is formed in which $R^2$ is an ester-forming group that can be hydrolyzed easily by a digestive tract esterase. For this purpose, the compound (I') obtained in the step 5 is subjected to esterification in the ordinary manner using an alkyl halide as a compound (8) as described, for example, in JP 89-316423. In the esterification reaction, acetonitrile, N,N-dimethylformamide, dimethylacetamide, acetone or the like may be used as a preferred solvent. The reaction may be carried out at a temperature in the range of from −40° C. to room temperature, preferably from −20° to 0° C. The reaction completes generally within 1 hour, though the reaction time varies depending on the reactivity of the compound (I'), the amount of an esterification agent to be used, reaction temperature to be employed, and the like. After completion of the reaction, the reaction mixture is subjected to ordinary post-treatments and, if necessary, the thus obtained compound (I) is purified by means of silica gel column chromatography or the like and isolated by precipitation, crystallization, or the like.

The cephalosporin derivative of the present invention represented by the general formula (I) is possessed of potent antibacterial activities upon various pathogenic bacteria and also has a property to give and maintain its concentration in blood at a high level after administration of the derivative.

The following describes these advantageous biological properties of the compound of the present invention, using typical examples of the compound.

TEST EXAMPLE 1

In this test example, antibacterial activities of the following typical examples of the compound (I) of the present invention upon various bacterial species are illustrated by showing their minimum growth inhibitory concentrations measured by the ordinary serial dilution technique. The measurement was made by inoculating $10^6$ CFU/ml of each test strain on a Sensitivity Plate Medium N (Nissui Pharmaceutical Co., Ltd.) and culturing the inoculated cells at 35° C. for 18 to 20 hours. Test Compounds:

(A): 7-{(Z)-2-(5-amino-1,2,4-thiadiazol-3-yl)-2-methoxyiminoacetamido}-3-(benzothiazol-2-yl)thio-3-cephem-4-carboxylic acid (B): 7-{(Z)-2-(5-amino-1,2,4-thiadiazol-3-yl)-2-methoxyiminoacetamido}-3-(thiazolo[5,4-b]pyridin-2-yl)thio-3-cephem-4-carboxylic acid Measured values of the minimum growth inhibitory concentration of the test compounds A and B are shown in Table 1 below.

TABLE 1

| Test Strain | Minimum Growth Inhibitory Concentration (μg/ml) | |
| --- | --- | --- |
| | Compound A | Compound B |
| Sta. aureus 209P JC-1 | 0.39 | 0.78 |
| Sta. aureus M 133 (*) | 1.56 | 3.13 |
| Sta. aureus M 126 (*) | 3.13 | 12.5 |
| Sta. epidermidis ATCC 14990 | 0.39 | 0.39 |
| E. coli NIHJ JC-2 | 3.13 | 3.13 |
| K. pneumoniae PCI 602 | 3.13 | 3.13 |
| P. vulgaris GN 76 | 3.13 | 12.5 |
| M. morganii 1510/S-1 | 1.56 | 50 |

Note: (*), methicillin-resistant *Staphylococcus aureus*

TEST EXAMPLE 2

This test example illustrates that the following typical examples of the compound of the present invention can give and maintain their concentrations in blood at high levels after subcutaneous injection. Test Compounds:

(A): 7-{(Z)-2-(5-amino-1,2, 4-thiadiazol-3-yl)-2-methoxyiminoacetamido}-3-(benzothiazol-2-yl)thio-3-cephem-4-carboxylic acid (B): 7-{(Z)-2-(5-amino-1,2, 4-thiadiazol-3-yl)-2-methoxyiminoacetamido}-3-(thiazolo [5,4-b]pyridin-2-yl) thio-3-cephem-4-carboxylic acid (C): 7-{(Z)-2-(2-aminothiazol-4-yl)- 2-methoxy-iminoacetamido}-3-(benzoxazol-2-yl)thio-3-cephem-4-carboxylic acid The test was carried out in the following manner. Using five male mice of ICR line (4 weeks old, 1 individual/group for blood collection), 0.5 mg of each test compound dissolved in 0.2 ml of sterile water for injection use was administered to each mouse by subcutaneous injection. Blood collection was carried out after 5 minutes, 15 minutes, 30 minutes, 1 hour and 2 hours after the administration. Each of the thus collected blood samples was subjected to ordinary post-treatment, and then serum concentration of the cephem compound was measured by making use of HPLC. Half-life period and AUC (area under the plasma concentration-time curve) as pharmacokinetic parameters were calculated in accordance with the Gauss-Newton method.

Measured values of the maximum concentration and half-life period of the test compounds A, B and C in blood are shown in Table 2 below, together with calculated AUC values.

TABLE 2

| | Compound A | Compound B | Compound C |
| --- | --- | --- | --- |
| Maximum concentration in blood (μg/ml) | 126.5 | 109.9 | 140.6 |
| Half-life period (hr) | 1.8 | 1.3 | 2.1 |
| AUC (μg · hr/ml) | 342.8 | 229.6 | 442.2 |

Since the cephalosporin derivative represented by the general formula (I) of the present invention shows potent antibacterial activity and high blood concentration as evident from these results, it can be used markedly effectively as a therapeutic drug for the treatment of infectious diseases caused by various pathogenic bacteria. When the compound (I) of the present invention is used as a therapeutic drug, it may be mixed with various desired additives such as fillers, binders and the like and then made into various dosage forms by the conventional techniques known in the art.

The following examples are provided to further illustrate the present invention, but the examples are for purpose of illustration only and are not to be construed to limit the scope of the invention.

TEST EXAMPLE 3

Acute toxicity ($LD_{50}$) of compound of Inventive Example 2 is 1 to 1.5 g/kg i.v. in mice.

INVENTIVE EXAMPLE 1

(a) Diphenylmethyl 7-phenylacetamido-3-(benzoxazol-2-yl)thio-3-cephem-4-carboxylate A 1.00 g portion of diphenylmethyl 7-phenylacetamido-3-trifluoromethylsulfonyloxy-3-cephem-4-carboxylate was suspended in 10 ml of methylene chloride and the suspension was cooled on an ice bath. To this was added 301 mg of 2-mercaptobenzoxazole sodium salt, followed by 6 hours of reaction at room temperature. After removing insoluble materials by filtration, the resulting organic layer was washed with 10 ml of saturated brine and then dried on anhydrous magnesium sulfate. After distilling off the solvent under a reduced pressure, the residue was purified by subjecting it to a column chromatography (60 g silica gel, toluene:ethyl acetate =6:1) and collecting fractions containing the compound of interest. Thereafter, the solvent was distilled off under a reduced pressure and the compound of interest was crystallized from a mixture solution of 5 ml ethyl acetate and 50 ml diisopropyl ether, thereby obtaining 327 mg of the title compound as white crystals (yield, 33%).

NMR (CDCl$_3$) δ ppm: 3.54 (1H, d, J=18Hz), 3.61 (1H, d, J=16Hz), 3.68 (1H, d, J=16Hz), 3.92 (1H, d, J=18Hz), 5.10 (1H, d, J=5Hz), 5.92 (1H, dd, J=5Hz, 9Hz), 6.15 (1H, d, J=9Hz), 6.96 (1H, s), 7.15–7.40 (17H, m), 7.45 (1H, m), 7.65 (1H, m)

(b) Diphenylmethyl 7-amino-3-(benzoxazol-2-yl)thio-3-cephem-4-carboxylate

A 327 mg portion of diphenylmethyl 7-phenylacetamido-3-(benzoxazol-2-yl)thio-3-cephem-4-carboxylate was dissolved in 4 ml of methylene chloride and the resulting solution was cooled to −15° C. To this were added 96 μl of pyridine and 161 mg of phosphorous pentachloride, followed by 1 hour of stirring at −5° C. Next, the reaction solution was cooled down to −20° C., mixed with 1.3 ml of methanol, and then stirred for 3 hours at −5° C. The resulting solution was mixed with 4 ml of water, stirred for additional 1 hour at the same temperature, and then subjected to liquid phase separation. The organic layer was mixed with 4 ml of water, adjusted to pH 7 with saturated sodium bicarbonate aqueous solution and then subjected to liquid phase separation. After drying the resulting organic layer on anhydrous magnesium sulfate and distilling off the solvent under a reduced pressure, the residue was purified by a column chromatography (20 g silica gel, toluene:ethyl acetate =2:1) to obtain 207 mg of the title compound (yield, 78%).

NMR (CDCl$_3$) δ ppm: 1.72 (2H, s), 3.56 (1H, d, J=18Hz), 3.90 (1H, d, J=18Hz), 4.85 (1H, d, J=5Hz), 5.04 (1H, d, J=5Hz), 6.98 (1H, s), 7.15–7.40 (12H, m), 7.45 (1H, m), 7.65 (1H, m)

(c) Diphenylmethyl 7-{(Z)-2-(2-tritylaminothiazol-4-yl)-2-methoxyiminoacetamido }-3-(benzoxazol-2-yl)thio-3-cephem-4-carboxylate A 207 mg portion of diphenylmethyl 7-amino-3-(benzoxazol-2-yl)thio-3-cephem-4-carboxylate was dissolved in 4 ml of methylene chloride and the resulting solution was cooled to −20° C. To this were added 213 mg of (Z)-2-(2-tritylaminothiazol-4-yl)-2-methoxyiminoaceticacid, 0.13 ml of pyridine and 45 μl of phosphorous oxychloride, followed by 20 minutes of stirring at the same temperature. The resulting solution was mixed with 4 ml of water, stirred for additional 1 hour at room temperature, and then subjected to organic layer separation. After drying the resulting organic layer on anhydrous magnesium sulfate and distilling off the solvent under a reduced pressure, the residue was purified by a column chromatography (30 g silica gel, toluene:ethyl acetate =3:1) to obtain 272 mg of the title compound (yield, 72%).

NMR (CDCl$_3$) δ ppm: 3.60 (1H, d, J=18Hz), 3.97 (1H, d, J=18Hz), 4.07 (3H, s), 5.20 (1H, d, J=5Hz), 6.01 (1H, dd, J=5Hz, 9Hz), 6.74 (1H, s), 6.85 (1H, d, J=9Hz), 6.98 (1H, s), 7.15–7.40 (26H, m), 7.45 (1H, m), 7.65 (1H, m)

(d) 7-{(Z)-2-(2-aminothiazol-4-yl)-2-methoxyiminoacetamido }-3-(benzoxazol-2-yl)thio-3-cephem-4-carboxylic acid A 272 mg portion of diphenylmethyl 7-{(Z)-2-(2-tritylaminothiazol-4-yl)-2-methoxyiminoacetamido }-3-(benzoxazol-2-yl)thio-3-cephem-4-carboxylate was dissolved in 1.4 ml of anisole. Under cooling on an ice bath, the resulting solution was mixed with 2.7 ml of trifluoroacetic acid and stirred for 30 minutes at the same temperature. The resulting reaction mixture was added dropwise to 14 ml of diisopropyl ether, and the formed precipitate was recovered by filtration and dried. The thus dried product was suspended in 3 ml of distilled water, and the suspension was adjusted to pH 7 with saturated sodium bicarbonate aqueous solution. Thereafter, this solution was chromatographed using 10 ml of HP-20 resin and freeze-dried to obtain 73 mg of the title compound as a sodium salt (yield, 46%).

NMR (CDCl$_3$) δ ppm: 3.44 (1H, d, J=18Hz), 3.86 (3H, s), 4.00 (1H, d, J=18Hz), 5.19 (1H, d, J=5Hz), 5.70 (1H, dd, J=5Hz, 9Hz), 6.73 (1H, s), 7.15 (2H, s), 7.31 (2H, m), 7.60 (2H, m), 9.63 (1H, d, J=9Hz)

INVENTIVE EXAMPLE 2

(a) Diphenylmethyl 7-phenylacetamido-3-(benzothiazol-2-yl)thio-2-cephem-4-carboxylate A 1.369 g portion of diphenylmethyl 7-phenylacetamido-3-trifluoromethylsulfonyloxy-3-cephem-4-carboxylate was dissolved in 14 ml of dichloromethane. Under cooling on an ice bath, to this were added 0.45 ml of N,N-diisopropylethylamine and 435 mg of 2-mercaptobenzothiazole, followed by 30 minutes of stirring at the same temperature. The resulting solution was washed with 14 ml of water and dried on anhydrous magnesium sulfate. After distilling off the solvent under a reduced pressure, the residue was purified by a column chromatography (150 g silica gel, toluene:ethyl acetate =6:1) to obtain 1.144 g of the title compound (yield, 81%).

NMR (CDCl$_3$) δ ppm: 3.67 (2H, ABq, J=17Hz), 5.30 (1H, d, J=5Hz), 5.46 (1H, d, J=2Hz), 5.61 (1H, dd, J=5Hz, 9Hz), 6.33 (1H, d, J=9Hz), 6.80 (1H, s), 7.09 (1H, d, J=2Hz), 7.15–7.45 (17H, m), 7.72 (1H, d, J=7Hz), 7.86 (1H, d, J=7Hz)

(b) Diphenylmethyl 7-phenylacetamido-3-(benzothiazol-2-yl)thio-3-cephem-4-carboxylate A 1.144 g portion of diphenylmethyl 7-phenylacetamido-3-(benzothiazol-2-yl)thio-2-cephem-4-carboxylate was dissolved in 11 ml of dichloromethane. Under cooling on an ice bath, to this was added dropwise 607 mg of metachloroperbenzoic acid which has been dissolved in 11 ml of dichloromethane, followed by 15 minutes of stirring at the same temperature. The resulting organic layer was washed with 11 ml of 5% sodium thiosulfate aqueous solution and then with 11 ml of saturated sodium bicarbonate aqueous solution, followed by drying on anhydrous magnesium sulfate and subsequent removal of the solvent by distillation under a reduced pressure.

The resulting residue was dissolved in 11 ml of N,N-dimethylformamide, mixed with 0.17 ml of phosphorous trichloride under cooling on an ice bath and then stirred for 10 minutes at the same temperature. The thus treated solution was mixed with 100 ml of ethyl acetate and 100 ml of 20% brine, and stirred for 30 minutes at room temperature, followed by liquid phase separation. The resulting organic layer was washed with 100 ml of 20% brine and dried on anhydrous magnesium sulfate. After distilling off the solvent under a reduced pressure, the residue was purified by a column chromatography (100 g silica gel, toluene:ethyl acetate=6:1) to obtain 612 mg of the title compound (yield, 53%).

NMR (CDCl$_3$) δ ppm: 3.56 (1H, d, J=18Hz), 3.64 (2H, ABq, J=17Hz), 3.86 (1H, d, J=18Hz), 5.07 (1H, d, J=5Hz), 5.91 (1H, dd, J=5Hz, 9Hz), 6.13 (1H, d, J=9Hz), 6.97 (1H, s), 7.20–7.50 (17H, m), 7.78 (1H, d, J=7Hz), 7.95 (1H, d, J=7Hz)

(c) Diphenylmethyl 7-amino-3-(benzothiazol-2-yl)thio-3-cephem-4-carboxylate

Using 824 mg of diphenylmethyl 7-phenylacetamido-3-(benzothiazol-2-yl)thio-3-cephem-4-carboxylate, the reaction and purification process of Inventive Example 1 (b) was repeated to obtain 499 mg of the title compound (yield, 74%).

NMR (CDCl$_3$) δ ppm: 1.78 (2H, br-s), 3.57 (1H, d, J=18Hz), 3.88 (1H, d, J=18Hz), 4.83 (1H, d, J=5Hz), 5.06 (1H, d, J=5Hz), 7.00 (1H, s), 7.15–7.50 (12H, m), 7.78 (1H, d, J=7Hz), 7.93 (1H, d, J=7Hz)

(d) Diphenylmethyl 7-{(Z)-2-(5-amino-1,2,4-thiadiazol-3-yl)-2-methoxyiminoacetamido }-3-(benzothiazol-2-yl)thio-3-cephem-4-carboxylate A 136 mg portion of (Z)-(5-amino-1,2, 4-thiadiazol-3-yl)-2-methoxyiminoacetic acid was dissolved in 2 ml of N,N-dimethylformamide, followed by the addition of 91 mg of hydroxybenzotriazole and 139 mg of dicyclohexylcarbodiimide. After 1.5 hours of stirring at room temperature, to the resulting solution was added 239 mg of diphenylmethyl 7-amino-3-(benzothiazol-2-yl) thio-3-cephem-4-carboxylate which has been dissolved in 3 ml of N,N-dimethylformamide, followed by 6 hours of stirring at room temperature. After the removal of insoluble materials by filtration, the resulting solution was mixed with 50 ml of ethyl acetate and 50 ml of 20% brine, and the mixture was subjected to liquid phase separation. The resulting organic layer was washed with 20% brine and dried on anhydrous magnesium sulfate. After distilling off the solvent under a reduced pressure, the residue was purified by a column chromatography (40 g silica gel, toluene:ethyl acetate=1:2) to obtain 324 mg of the title compound (yield, 100%).

NMR (CDCl$_3$) δ ppm: 3.55 (1H, d, J=18Hz), 3.94 (1H, d, J=18Hz), 4.05 (3H, s), 5.22 (1H, d, J=5Hz), 6.18 (1H, dd, J=5Hz, 9Hz), 6.34 (2H, s), 6.99 (1H, s), 7.15–7.50 (12H, m), 7.79 (1H, d, J=8Hz), 7.95 (1H, d, J=8Hz), 8.13 (1H, d, J=9Hz)

(e) 7-{(Z)-2-(5-amino-1,2,4-thiadiazol-3-yl)-2-methoxyiminoacetamido}-3-(benzothiazol-2-yl)thio-3-cephem-4-carboxylic acid Using 324 mg of diphenylmethyl 7-{(Z)-2-(5-amino-1,2,4-thiadiazol-3-yl)-2-methoxyiminoacetamido}-3-(benzothiazol-2-yl)thio-3-cephem-4-carboxylate, the reaction and purification process of Inventive Example 1 (d) was repeated to obtain 137 mg of the title compound as a sodium salt (yield, 64%).

NMR (DMSO-d$_6$) δ ppm: 3.37 (1H, d, J=18Hz), 3.90 (1H, d, J=18Hz), 3.92 (3H, s), 5.17 (1H, d, J=5Hz), 5.72 (1H, d, J=5Hz, 9Hz), 7.32 (1H, t, J=8Hz), 7.42 (1H, t, J=8Hz), 7.80 (1H, d, J=5Hz), 7.94 (1H, d, J=8Hz), 8.10 (2H, s), 9.65 (1H, d, J=9Hz)

INVENTIVE EXAMPLE 3

(a) Diphenylmethyl 7-phenylacetamido-3-(pyridino [5,4b]thiazol-2-yl)thio-2-cephem-4-carboxylate Using 1.369 g of diphenylmethyl 7-phenyl-acetamido-3-trifluoromethanesulfonyloxy-2-cephem-4-carboxylate, the reaction and purification process of Inventive Example 2 (a) was repeated to obtain 1.143 g of title compound (yield, 81%).

NMR (CDCl$_3$) δ ppm: 3.64 (1H, d, J=16Hz), 3.69 (1H, d, J=16Hz), 5.31 (1H, d, J=5Hz), 5.51 (1H, s), 5.59 (1H, dd, J=5Hz, 9Hz), 6.39 (1H, d, J=9Hz), 6.81 (1H, s), 7.10 (1H, s), 7.15–7.40 (16H, m), 8.02 (1H, d, J=8Hz), 8.45 (1H, d, J=4Hz)

(b) Diphenylmethyl 7-phenylacetamido-3-(pyridino [5,4-b]-thiazol-2-yl)thio-3-cephem-4-carboxylate Using 1.143 g of diphenylmethyl 7-phenylacetamido-3-(pyridino[5,4-b]thiazol-2-yl)thio-2-cephem-4-carboxylate, the reaction and purification process of Inventive Example 2 (b) was repeated to obtain 612 mg of title compound (yield, 53%).

NMR (CDCl$_3$) δ ppm: 3.55 (1H, d, J=18Hz), 3.62 (1H, d, J=16Hz), 3.69 (1H, d, J=16Hz), 3.92 (1H, d, J=18Hz), 5.10 (1H, d, J=5Hz), 5.93 (1H, dd, J=5Hz, 9Hz), 6.10 (1H, d, J=9Hz), 6.97 (1H, s), 7.15–7.45 (16H, m), 8.10 (1H, d, J=8Hz), 8.52 (1H, d, J=4Hz)

(c) Diphenylmethyl 7-amino-3-(pyridino[5,4-b]thiazol-2-yl)thio-3-cephem-4-carboxylate Using 612 mg of diphenylmethyl 7-phenylacetamido-3-(pyridino [5,4-b]thiazol-2-yl)thio-3-cephem-4-the reaction and purification process of Inventive Example 1 (b) was repeated to obtain 298 mg of title compound (yield, 60%).

NMR (CDCl$_3$) δ ppm: 1.65 (2H, s), 3.60 (1H, d, J=18Hz), 3.93 (1H, d, J=18Hz), 4.85 (1H, d, J=5Hz), 5.09 (1H, d, J=5Hz), 7.00 (1H, s), 7.15–7.35 (10H, m), 7.40 (1H, dd, J=8Hz, 4Hz), 8.10 (1H, d, J=8Hz), 8.51 (1H, d, J=4Hz)

(d) Diphenylmethyl 7-{(Z)-2-(5-amino-1,2,4-thiadiazol-3-yl)-2-methoxyiminoacetamido}-3-(thiazolo [5,4-b]pyridin-2-yl)thio-3-cephem-4-carboxylate Using 298 mg of diphenylmethyl 7-amino-3-(thiazolo[5,4-b]pyridin-2-yl)thio-3-cephem-4-carboxylate, the reaction and purification process of Inventive Example 2 (d) was repeated to obtain 335 mg of the title compound (yield, 84%).

NMR (CDCl$_3$) δ ppm: 3.59 (1H, d, J=18Hz), 3.96 (1H, d, J=18Hz), 4.06 (1H, s), 5.24 (1H, d, J=5Hz), 6.18 (1H, dd, J=5Hz, 9Hz), 6.54 (2H, s), 6.97 (1H, s), 7.10–7.40 (11H, m), 8.10 (1H, d, J=8Hz), 8.30 (1H, d, J=9Hz), 8.39 (1H, d, J=4Hz)

(e) 7-{(Z)-2-(5-amino-1,2,4-thiadiazol-3-yl)-2-methoxyiminoacetamido}-3-(thiazolo[5,4-b]pyridin-2-yl)thio-3-cephem-4-carboxylic acid Using 335 mg of diphenylmethyl 7-{(Z)-2-(5-amino1,2,4-thiadiazol-3-yl)-2-methoxyiminoacetamido}-3-(thiazolo [5,4-b]pyridin-2-yl)thio-3-cephem-4-carboxylate, the reaction and purification process of Inventive Example 1 (d) was repeated to obtain 187 mg of the title compound as a sodium salt (yield, 70%).

NMR (DMSO-d$_6$) δ ppm: 3.40 (1H, d, J=18Hz), 3.93 (3H, s), 3.96 (1H, d, J=18Hz), 5.20 (1H, d, J=5Hz), 5.75 (1H, dd, J=5Hz, 9Hz), 7.47 (1H, dd, J=8Hz, 4Hz), 8.10 (2H, s), 8.13 (1H, d, J=8Hz), 8.45 (1H, d, J=4Hz), 9.68 (1H, d, J=9Hz)

While the invention has been described in detail and with reference to specific embodiments thereof, it will be apparent to one skilled in the art that various changes and modifications can be made therein without departing from the spirit and scope thereof.

What is claimed is:

1. A cephalosporin derivative represented by the following formula (I) or a pharmaceutically acceptable salt thereof:

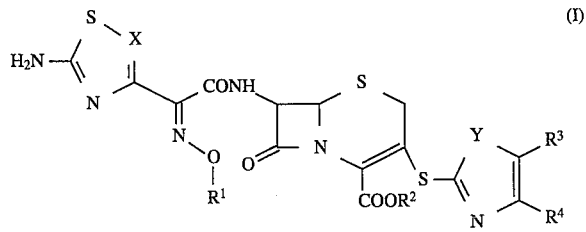

wherein when X is a carbon atom, Y is an oxygen atom, $R^1$ is a hydrogen atom or a lower alkyl, $R^2$ is a hydrogen atom and $R^3$ and $R^4$, together, form a benezene ring, or wherein when X is a nitrogen atom, Y is a sulfur atom or an oxygen atom, $R^1$ is a hydrogen atom or a lower alkyl, $R^2$ is a hydrogen atom and $R^3$ and $R^4$, together, form a benezene ring or a 6-membered heterocyclic ring having 1 nitrogen atom.

2. An antibacterial composition comprising a pharmaceutically acceptable carrier, and as an active ingredient, a cephalosporin derivative represented by the following formula (I) or a pharmaceutically acceptable salt thereof:

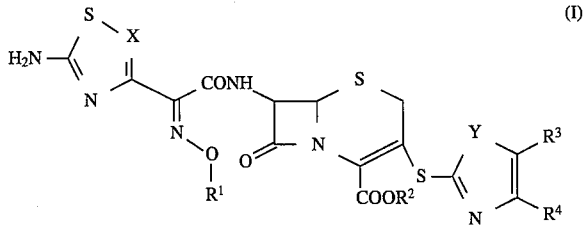

wherein when X is a carbon atom, Y is an oxygen atom, $R^1$ is a hydrogen atom or a lower alkyl, $R^2$ is a hydrogen atom and $R^3$ and $R^4$, together, form a benezene ring, or wherein when X is a nitrogen atom, Y is a sulfur atom or an oxygen atom, $R^1$ is a hydrogen atom or a lower alkyl, $R^2$ is a hydrogen atom and $R^3$ and $R^4$, together, form a benezene ring or a 6-membered heterocyclic ring having 1 nitrogen atom.

* * * * *